(12) United States Patent
Van Saarloos et al.

(10) Patent No.: US 6,369,898 B1
(45) Date of Patent: Apr. 9, 2002

(54) METHOD AND APPARATUS FOR SURFACE PROFILING OF MATERIALS AND CALIBRATION OF ABLATION LASERS

(75) Inventors: Paul Phillip Van Saarloos, Karrinyup (AU); David Clyde MacPherson, Conifer, CO (US)

(73) Assignee: Q-Vis Limited (AU)

( * ) Notice: Subject to any disclaimer, the term of this patent is extended or adjusted under 35 U.S.C. 154(b) by 0 days.

(21) Appl. No.: 09/484,773

(22) Filed: Jan. 18, 2000

(Under 37 CFR 1.47)

Related U.S. Application Data

(63) Continuation of application No. PCT/AU98/00568, filed on Jul. 17, 1998.

(30) Foreign Application Priority Data

Jul. 18, 1997 (AU) ............................................. PO8109

(51) Int. Cl.$^7$ ................................................. G01B 9/02
(52) U.S. Cl. .................................................... 356/497
(58) Field of Search ............................ 356/479, 497; 351/212; 606/5

(56) References Cited

U.S. PATENT DOCUMENTS

| | | |
|---|---|---|
| 4,710,001 A | 12/1987 | Lacey |
| 5,261,822 A | 11/1993 | Hall et al. |
| 5,490,849 A | 2/1996 | Smith |
| 5,493,109 A | 2/1996 | Wei et al. |
| 5,579,112 A | * 11/1996 | Sugiyama et al. .......... 356/497 |
| 5,659,392 A | * 8/1997 | Marcus et al. .............. 356/479 |
| 6,116,737 A | * 9/2000 | Kern .......................... 351/212 |

FOREIGN PATENT DOCUMENTS

EP 0342289 11/1989

OTHER PUBLICATIONS

Saarloos and Constable, J. Appl. Phys. 68(i), (1990), p. 377.

* cited by examiner

*Primary Examiner*—Samuel A. Turner
(74) *Attorney, Agent, or Firm*—Baker Botts LLP

(57) ABSTRACT

Method and apparatus are provided for measuring the surface profile of a sample. The method and apparatus provide light from a light source through a beam splitter to form two split beams, direct the split beams onto a sample surface and a reference surface respectively, reflect the split beams back through the beam splitter, and direct the split beams towards an imaging system. A surface profiling apparatus for measuring the surface profile of the sample is also provided. The apparatus includes a light source for generating a source beam, beam splitting means positioned in the path of the source beam for splitting the source beam into split beams, a reference surface, a sample surface allowing the split beams to traverse separate paths and return to the beam splitting means, reference surface positioning means for positioning the reference surface, and viewing means for imaging combined beams. An apparatus for calibrating a laser for the ablation of a material including the surface profiling apparatus is also provided.

81 Claims, 2 Drawing Sheets

METHOD AND APPARATUS FOR SURFACE PROFILING OF MATERIALS AND CALIBRATION OF ABLATION LASERS

This is a continuation of copending International application No. PCT/AU98/00568 filed Jul. 17, 1998.

The present invention relates to the surface profiling of materials, for example as in the laser processing or ablation of materials, or as needed in the calibration and performance checking of the laser apparatus used in operations on the corneal tissue of the eye for the correction of refractive errors.

The invention will be described by reference to two operations for the correction of refractive errors, photorefractive keratectomy (PRK) and laser in-situ keratomeleusis (LASIK), but the invention may be used to measure the surface profile of a wide range of materials or to calibrate lasers for a variety of medical and industrial applications.

To ensure that the correct profile is etched onto a patient's cornea during PRK or LASIK, the surgical laser must first be calibrated. This process imparts an accurate picture of how the laser will ablate the cornea. The corneal surface may be ablated to effect a myopic, hyperopic or astigmatic correction. Myopic corrections should produce a new, flatter curvature, while hyperopic corrections should remove more material around the edge of the area to be ablated.

One of the current methods used to perform the calibration procedure involves etching the surface of a plastic polymer such as polymethyl-methacrylate (PMMA). The etched surface is examined by an instrument known as a lensometer. This instrument determines the power of the resultant 'lens' in diopters. The reading can then be compared to the desired refractive correction. Discrepancies between the desired and achieved readings indicate that the laser needs to be adjusted, by a factor proportional to the difference between the lensometer reading and the desired surgical correction (see U.S. Pat. No. 5,261,822).

Another method of calibration is described in U.S. Pat. No. 5,261,822. This patent illustrates the use of a calibration block that can be examined by visual inspection. It teaches the use of a plurality of thin coatings of PMMA of progressively increasing thickness, layered over a solid substrate of the same material. Each layer may be doped with a differently coloured or fluorescent material. When the cavity of material ablated by the laser is viewed from above, a pattern of circles is visible. A correctly calibrated laser should produce patterns of concentric circles, whereas patterns of eccentric circles indicate that the laser is not correctly calibrated. However, the result is usually judged subjectively and this technique provides only a crude prediction of the shape created during a refractive correction.

The above laser calibration methods suffer from a number of disadvantages. PMMA does not necessarily mimic the ablation characteristics of corneal tissue, and different brands of PMMA ablate at different rates (P.P. van Saarloos and I. J. Constable, J. Appl. Phys. 68(1) (1990) 377). Further, different brands of lasers ablate at different fluences, where the ratio of ablation rates of tissue and plastic are different. Nor does the lensometer provide an accurate reading of the ablation surface. The shape desired to be etched on the cornea does not necessarily produce an accurate lens shape when ablated into plastic. The ablated surface is usually aspheric, and may be inaccurately read. This means that a lensometer reading does not give an absolute measure of laser performance, and in some cases the measurement is meaningless. This method can therefore only give an approximate reading of surface curvature. Lensometer readings are also time consuming.

Other known methods to measure ablated surface profiles include the use of interferometry, or include scanning the ablated surface with a scanning electron microscope, a confocal microscope or surface contact needles. Devices according to these known methods are, however, costly and of prohibitive size, and impractical to cover the range of shapes produced by refractive lasers. There exists, therefore, a demand for an accurate, low cost device for performance analysis and calibration of refractive lasers to ensure appropriate shapes are etched onto the surface to be ablated.

It is an object of the present invention to provide a new and improved method and apparatus for surface profiling of materials and calibration of ablation lasers that can more accurately and reliably examine the surface of an ablation.

According to the present invention, therefore, there is provided a method for measuring the surface profile of a sample, said method including:

directing light from a light source through a beam splitter to form two split beams;

directing said split beams onto a sample surface and a reference surface respectively;

reflecting the split beams back through the beam splitter; and directing said split beams towards an imaging system.

Preferably the method is for use in calibrating a laser ablation apparatus for ablation of a material by measuring the result of an ablation of the sample.

The method may include reflecting said light from a mirror and/or focussing said light to minimise space requirements.

Preferably the light source includes a light emitting diode.

Alternatively the light source is a source of white or near infra-red light.

Preferably the sample surface is a plastic polymer that ablates at a substantially constant fraction of the ablation rate of said material over the range of fluences used in ablating said material, and preferably the fraction equals 1.0.

The material may be biological material.

The biological tissue may be corneal tissue, and the method include ablating said material in a surgical procedure, in which case the fluences are preferably in the range 50–800 mJ/cm$^2$, and more preferably in the range 120–250 mJ/cm$^2$.

Preferably the reference surface is a flat mirror or a flat surface.

The reference surface may be mounted on a pendulum including a plurality of substantially parallel sheets of flexible material.

The method may include moving the reference surface by means of a speaker or voice coil.

Preferably the imaging system includes a CCD video camera.

The method may include measuring said surface profile, comparing said measurement with a predicted profile, and determining an indicator of the safety or predictability of ablation performed on said sample for use in a surgical procedure.

Preferably the reference surface positioning means includes a voice coil driver and a position sensor.

The method may include transferring the calibration profile information ascertained by said method into a laser system control computing device, to allow the self correction of the calibration and shape controls of the laser system.

The method may also include communicating with a topography measuring device for measuring the topography of the front surface of a human or animal eye in order to combine the results of a calibration measurement in plastic and the results of a topography measurement, and predicting from said calibration and topography results the post laser treatment shape of the eye.

The present invention also provides a surface profiling apparatus for measuring the surface profile of a sample, the apparatus including:

a light source for generating a source beam;

beam splitting means positioned in the path of the source beam for splitting said source beam into split beams;

a reference surface;

a sample surface allowing said split beams to traverse separate paths and return to said beam splitting means;

reference surface positioning means for positioning the reference surface; and viewing means for imaging combined beams.

The apparatus may include focussing optical elements to concentrate the intensity of said light, and a mirror, said optical elements and said mirror located between said light source and said beam splitting means.

Preferably the light is white light or near infra-red light.

The light source may include a halogen bulb, or a light emitting diode (LED).

Preferably said LED has a maximum intensity in the red to infra-red portion of the spectrum.

The reference surface may be a flat mirror or a flat surface.

The imaging system preferably includes a CCD video camera.

Preferably the reference surface positioning means includes a voice coil driver and a position sensor.

Preferably the position sensor includes a known sample.

Preferably the position sensor includes a mirror or optical element that allows both the known sample and the plastic sample being measured to be viewed by means of the imaging system simultaneously or alternately.

In one form of the invention, the position sensor is a capacitance or inductance position sensor.

Preferably the voice coil driver is similar to that used in a loud-speaker.

The position sensor may be an opto-electric sensor including a photodiode with an amplification system and an additional LED, wherein the sensor uses the intensity of the additional LED, and said additional LED is positioned to reflect light at an angle from the reference surface, or any surface moving with the reference surface, to the photodiode.

Preferably the position sensor is one of a plurality of position sensors.

Preferably the plurality of position sensors includes a plurality of types of position sensor.

In one embodiment, the reference surface positioning means includes a loud-speaker.

Preferably the loud-speaker is used as or constitutes a displacement driver for the reference surface.

Preferably the reference surface is mounted on a pendulum including a plurality of substantially parallel sheets of flexible material.

The invention also provides an apparatus for calibrating a laser for the ablation of a material including the surface profiling apparatus described above.

The sample surface may comprise a plastic polymer that ablates at a substantially constant fraction of the ablation rate of said material over the range of fluences used in ablating said material, and preferably the fraction equals 1.0.

The material may be biological material, including for example corneal tissue, and the apparatus may be for ablating the material in a surgical procedure (such as PRK or LASIK). In these cases the fluences are preferably in the range 50–800 mJ/cm$^2$ and more preferably in the range 120–250 mJ/cm$^2$.

In one particular embodiment, the apparatus includes a laser means, wherein the apparatus is for calibrating and/or checking the laser means, and includes communication means for communicating with, a computer controlled laser means, whereby the laser means can use calibration profile information obtained by the calibration apparatus to self correct the calibration and shape controls of said laser means. In this embodiment, the laser means may be for use in PRK or LASIK operations of the cornea of the eye to correct refractive errors.

The apparatus may include a corneal topography measuring means for measuring the topography of the front surface of a human or animal eye and communication means for communicating with said topography measuring means, for predicting post laser treatment eye topography from calibration measurements in plastic and topography measurements of the eye, and may further include display means for displaying the post laser treatment corneal topography predicted by means of the apparatus.

In order that the invention may be more fully explained, some preferred embodiments will be described, by way of example, with reference to the accompanying drawings in which:

FIGS. 1A and 1B show a typical myopic or myopic/astigmatic ablation pattern etched onto the surface of a plastic sample surface. The ablation pattern may have been etched by an excimer, solid state or other type of laser suitable for refractive correction.

Figure 2:
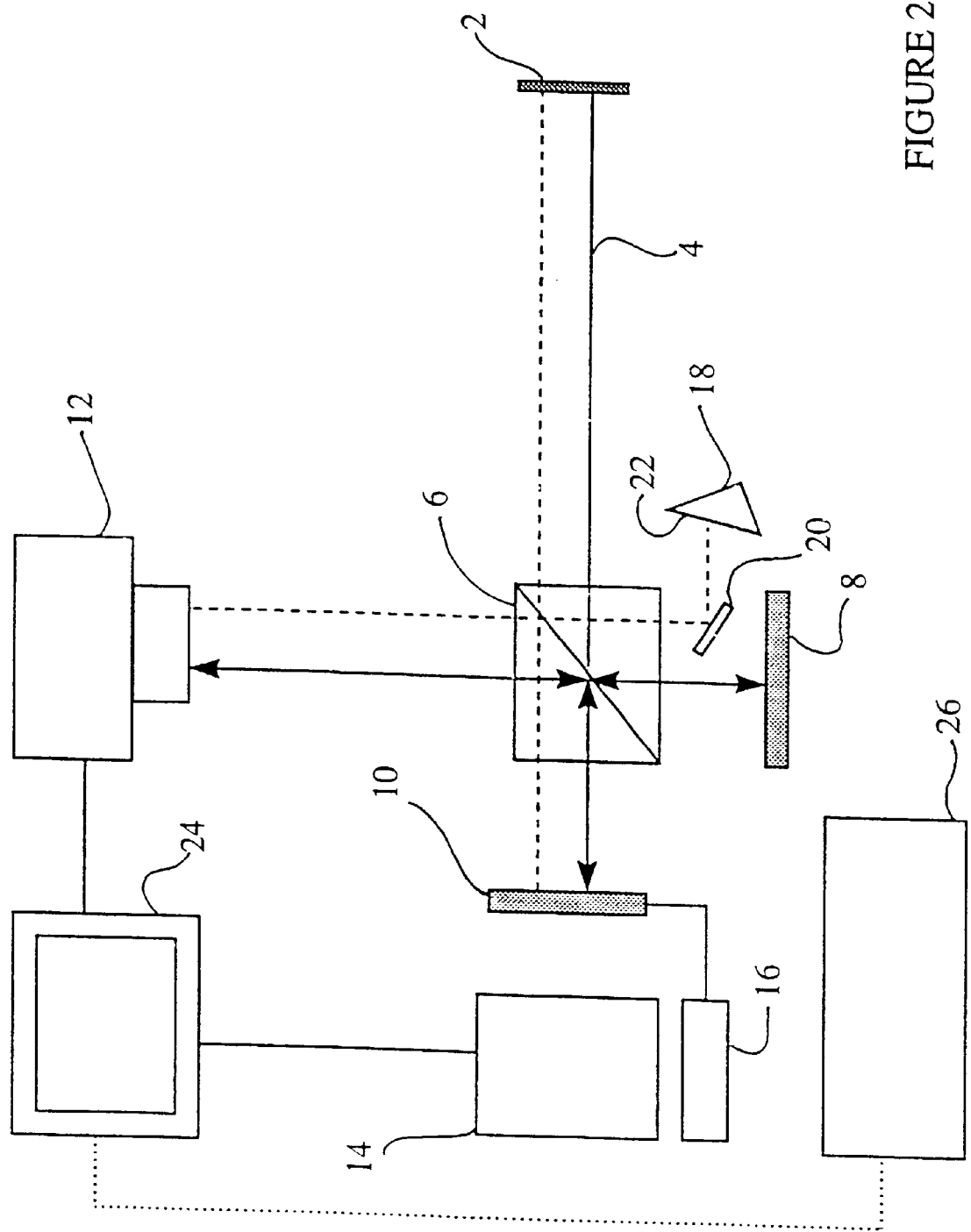
FIG. 2 is a schematic view of a calibration apparatus according to a preferred embodiment of the present invention.

Referring to FIG. 2, the first arrangement of the apparatus includes a red light source in the form of light emitting diode 2. Alternatively the light source may be a general purpose halogen bulb. The light 4 passes through a beam splitter 6 where two separate beams are formed. Some of the light is directed onto the ablated sample 8, which is a plastic polymer that ablates at the same rate as corneal tissue over the range of laser fluences used in corneal ablation procedures, 120 to 250 mJ/cm$^2$. The rest of the light is directed onto a reference surface 10 comprising a mirror or other flat surface which is scanned back and forth. Both the ablated plastic sample 8 and the reference surface 10 reflect or scatter the light back to the beam splitter 6. Some of the reflections from the sample 8 and the reference surface 10 bounce off the beam splitter 6 and disappear. The remaining combined beam is directed through the beam splitter 6 towards a CCD video camera 12, for example a COHO 11C0 video camera or the like. The reference surface 10 is scanned to adjust the beam path length of the light going back to the camera 12. When the light beam path length from the sample surface 8 matches the path length to the reference surface 10, interference patterns will be formed.

Figure 1B:
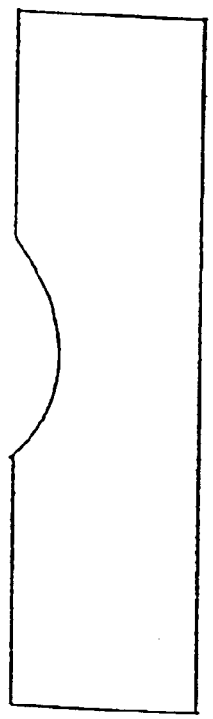
FIG. 1B is a cross section through A—A of FIG. 1A.
Figure 1A:
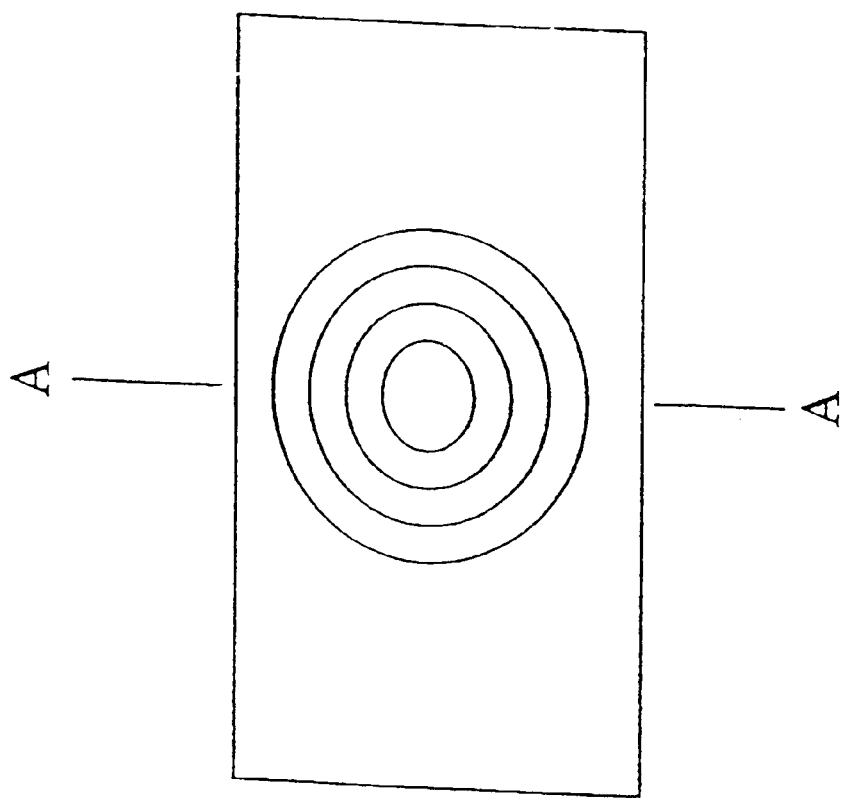
FIG. 1A is a diagrammatic plan view of an ablation pattern formed by a laser source directed onto the surface of a plastic sample surface.

For an ablated sample such as that of FIG. 1, when viewed through the camera 12, circular interference patterns are imaged for good, non-astigmatic, myopic ablations. A smaller circular pattern is produced at the deepest point of the ablated surface, when the reference surface 10 is further away from the beam splitter 6. Progressively larger circular patterns are produced as shallower ablations are encountered.

However, interference patterns can only be produced when the reference surface 10 and a point on the ablated sample 8 are at the same optical path distance from the video camera 12. The reference surface 10 must therefore be movable to allow the imaging of different ablation depths. A voice coil driver 14 moves the reference surface 10 back and forth, while an opto-electronic sensor 16 (or, in other embodiments, a capacitance or inductance position sensor), such as a photodiode with an amplification system, senses the spatial positioning of the reference surface 10. Voice coil driver 14 and position sensor 16 therefore allow positioning, with feedback from the reference surface 10 in relation to the ablated sample 8.

An alternative embodiment involves the use of optical rather than mechanical position measurement. In this embodiment, a known sample in the form of a wedge shaped object 18, and a small mirror 20, are used to detect the positioning of the reference surface 10. Voice coil 14 is again used to drive the reference surface 10. In this embodiment, the known sample 18 features a sloping surface 22 that reflects the minimum and maximum movement of the reference surface 10. However, position sensor 16 may additionally be used in this embodiment.

The calibration device as described above is preferably connected to a computer 24. This computer 24 can calculate the shape of the ablated sample surface 8, display the shape in a three dimensional form, compare the actual shape to a desired shape and issue a "go/no go" message, indicating that a good calibration or a laser problem has been detected, respectively. The computer may also be joined to a laser system or corneal topography device 26. The calibration device can therefore exchange information concerning the ablated profile with the laser system. The information provided about the measured profile produced can then be interpreted, and used to alter the parameters of the laser system so that the desired corneal profile is produced in its next ablation.

Apparatus for performing topographic profiling of the cornea may also be included in a preferred embodiment. This apparatus may be used to measure the original profile of a corneal surface and then import the measured ablation profile from the calibration apparatus of the present invention. The corneal topography that may be expected if a laser ablation procedure were performed on a cornea, based on the calibration data, may then be calculated and displayed. Alternatively, the calibration apparatus may read the corneal topographic data, and calculate and display on computer 24 the resultant corneal shape that would be created if the laser was used on the eye.

Thus, the present invention may be used to calibrate lasers used, for example, in the improvement of eyesight or other medical, dental or cosmetic procedures where the accurate ablation of tissue is required.

Modifications within the spirit and scope of the invention may be readily effected by a person skilled in the art. Such modifications may include swapping positions of the sample and reference surfaces. It is to be understood, therefore, that this invention is not limited to the particular embodiments described by way of example hereinabove.

What is claimed is:

1. A method for calibrating laser ablation apparatus, including:
   ablating a sample; measuring the surface profile of said sample by:
   directing light from a light source through a beamsplitter to form two split beams;
   directing said split beams respectively onto the ablated surface of said sample and also onto a reference surface;
   reflecting the split beams from said ablated surface and said reference surface, respectively, and forming an interference signal from said reflected split beams; and
   detecting said interference signal and therefrom determining the surface profile of said sample surface; and
   calibrating said laser ablation apparatus on the basis of said determined surface profile.

2. A method as claimed in claim 1, wherein said sample surface is a plastic polymer.

3. A method as claimed in claim 1, including reflecting said light from a mirror and/or focussing said light to minimise space requirements.

4. A method as claimed in claim 1, wherein said light source includes a light emitting diode.

5. A method as claimed in claim 1, wherein said light source is a source of white or near infra-red light.

6. A method according to in claim 1 for calibrating said apparatus for use in ablating a predetermined material, wherein said sample has an ablation rate that is a substantially constant fraction of the ablation rate of said material to be ablated over the range of fluences used in ablating said material.

7. A method as claimed in claim 6, wherein said fraction equals 1.0.

8. A method as claimed in claim 6, wherein said material is biological tissue.

9. A method as claimed in claim 8, wherein said biological tissue is corneal tissue.

10. A method as claimed in claim 8, in combination with the further step of ablating said material in a surgical procedure.

11. A method as claimed in claim 8, wherein said biological tissue is corneal tissue and said fluences are in the range 50–800 $mJ/cm^2$.

12. A method as claimed in claim 11, wherein said fluences are in the range 120–250 $mJ/cm^2$.

13. A method as claimed in claim 1, wherein said reference surface is a flat mirror or a flat surface.

14. A method as claimed in claim 1, wherein said reference surface is mounted on a pendulum including a plurality of substantially parallel sheets of flexible material.

15. A method as claimed in claim 1, including moving said reference surface by means of a speaker or voice coil.

16. A method as claimed in claim 1, wherein said interference signal is detected with an imaging system that includes a CCD video camera.

17. A method as claimed in claim 1, including measuring said surface profile, comparing said measurement with a predicted profile, and determining an indicator of the safety or predicability of ablation performed on said sample for use in a surgical procedure.

18. A method as claimed in claim 1, including adjusting the calibration and shape controls of the laser ablation apparatus.

19. A method as claimed in claim 1, including communicating with a topography measuring device for measuring the topography of the front surface of a human or animal eye in order to combine the results of a calibration measurement in plastic and the results of a topography measurement, and predicting from said calibration and topography results the post laser treatment shape of the eye.

20. A method according to claim 1 wherein said reflected split beams are directed back through said beamsplitter means to form said interference signal.

21. An apparatus for calibrating laser ablation apparatus, comprising:

a light source for generating a source beam;

beam-splitter means positioned in the path of the source beam for splitting said source beam into split beams;

a reference surface positioned to reflect one of said split beams back to said beamsplitter means for forming an interference signal with another of said split beams reflected back to said beamsplitter means by a surface of a sample ablated by said laser ablation apparatus;

reference surface positioning means including a voice coil driver for positioning the reference surface;

means to detect the position of said reference surface, to which detection means the voice coil driver is responsive;

means for imaging said interference signal; and means for determining, from said imaged interference signal, the surface profile of said sample surface and for calibrating said laser ablation apparatus on the basis of said determined surface profile.

22. An apparatus as claimed in claim 21 including focusing optical elements to concentrate the intensity of said source beam, and a mirror, said optical elements and said mirror located between said light source and said beamsplitter means.

23. An apparatus as claimed in claim 21, wherein said light source provides white light or near infra-red light.

24. An apparatus as claimed in claim 21, wherein said light source includes a halogen bulb, or a light emitting diode (LED).

25. An apparatus as claimed in claim 24, wherein said LED has a maximum intensity in the red to infra-red portion of the spectrum.

26. An apparatus as claimed in claim 21, wherein said reference surface is a flat mirror or a flat surface.

27. An apparatus as claimed in claim 21, wherein said imaging means includes a CCD video camera.

28. An apparatus as claimed in claim 21, wherein said position detection means includes a known sample.

29. An apparatus as claimed in claim 28, wherein said position detection means includes a mirror or optical element that allows both the known sample and said sample being measured to be viewed by means of the imaging system simultaneously or alternately.

30. An apparatus as claimed in claim 21, wherein said position sensor is a capacitance or inductance position sensor.

31. An apparatus as claimed in claim 21, wherein said voice coil driver is similar to that used in a loud-speaker.

32. An apparatus as claimed in claim 21, wherein said position detection means is an opto-electric sensor including a photodiode with an amplification system and an additional LED, wherein the sensor uses the intensity of the additional LED, and said additional LED is positioned to reflect light at an angle from the reference surface, or any surface moving with the reference surface, to the photodiode.

33. An apparatus as claimed in claim 21, wherein said position detection means comprises a plurality of position sensors.

34. An apparatus as claimed in claim 33, wherein said plurality of position sensors includes a plurality of types of position sensor.

35. An apparatus as claimed in claim 21, wherein said reference surface positioning means includes a loud-speaker.

36. An apparatus as claimed in claim 35, wherein said loud-speaker is used as or constitutes a displacement driver for the reference surface.

37. An apparatus as claimed in claim 21, wherein the reference surface is mounted on a pendulum including a plurality of substantially parallel sheets of flexible material.

38. An apparatus as claimed in claim 21, further including said sample, wherein said sample surface comprises a plastic polymer.

39. An apparatus as claimed in claim 38 for calibrating said laser ablation apparatus for use in ablating a predetermined material, wherein said sample has an ablation rate that is a substantially constant fraction of the ablation rate of said material to be ablated over the range of fluences used in ablating said material.

40. An apparatus as claimed in claim 39 wherein said material is biological tissue.

41. An apparatus as claimed in claim 40, wherein said biological tissue is corneal tissue.

42. an apparatus is claimed in claim 40, in combination with apparatus for laser ablating said biological tissue in a surgical procedure.

43. An apparatus as claimed in claim 42, wherein said surgical procedure is PRK or LASIK.

44. An apparatus as claimed in claim 40, wherein said fluences are in the range 50–800 mJ/cm$^2$.

45. An apparatus as claimed in claim 44, wherein said fluences are in the range 120–250 mJ/cm$^2$.

46. An apparatus as claimed in claim 21, including laser ablation apparatus, said means for determining said surface profile and for calibrating said laser ablation apparatus being in communication with said laser ablation apparatus for adjusting the calibration and shape controls thereof.

47. An apparatus as claimed in claim 21, including a corneal topography measuring means for measuring the topography of the front surface of a human or animal eye and communication means for communicating with said topography measuring means, for predicting post laser treatment eye topography from calibration measurements in plastic and topography measurements of the eye.

48. An apparatus as claimed in claim 21, including a corneal topography measuring means for measuring the topography of the front surface of a human or animal eye and communication means for communicating with said topography measuring means, for predicting post laser treatment eye topography from calibration measurements in plastic and topography measurements of the eye.

49. An apparatus as claimed in claim 48, including display means for displaying the post laser treatment corneal topography predicted by means of the apparatus.

50. Apparatus for calibrating laser ablation apparatus, comprising:

a light source for generating a source beam:

beamsplitter means positioned in the path of the source beam for splitting said source beam into split beams;

a reference surface positioned to reflect one of said split beams for forming an interference signal with another of said split beams reflected by a surface of a sample ablated by said laser ablation apparatus;

reference surface positioning means for positioning the reference surface;

means for imaging said interference signal; and means for determining, from said imaged interference signal, the surface profile of said sample surface and for calibrating said laser ablation apparatus on the basis of said determined surface profile.

51. An apparatus as claimed in claim 50, including focussing optical elements to concentrate the intensity of said light, and a mirror, said optical elements and said mirror located between said light source and said beam-splitter means.

52. An apparatus as claimed in claim 50, wherein said light source provides white light or near infra-red light.

53. An apparatus as claimed in claim 50, wherein said light source includes a halogen bulb, or a light emitting diode (LED).

54. An apparatus as claimed in claim 53, wherein said LED has a maximum intensity in the red to infra-red portion of the spectrum.

55. An apparatus as claimed in any one of claim 50, wherein said reference surface is a flat mirror or a flat surface.

56. An apparatus as claimed in claim 50, wherein said imaging means includes a CCD video camera.

57. An apparatus as claimed in claim 50, wherein said reference surface positioning means further includes a position sensor.

58. An apparatus as claimed in claim 57, wherein said position sensor includes a known sample.

59. An apparatus as claimed in claim 58, wherein said position sensor includes a mirror or optical element that allows both the known sample and said sample being measured to be viewed by means of the imaging system simultaneously or alternately.

60. An apparatus as claimed in claim 57, wherein said position sensor is a capacitance or inductance position sensor.

61. An apparatus as claimed in claim 57, wherein said position sensor is an opto-electric sensor including a photodiode with an amplification system and an additional LED, wherein the sensor uses the intensity of the additional LED, and said additional LED is positioned to reflect light at an angle from the reference surface, or any surface moving with the reference surface, to the photodiode.

62. An apparatus as claimed in claim 57, wherein said position sensor is one of a plurality of position sensors.

63. An apparatus as claimed in claim 62, wherein said plurality of position sensors includes a plurality of types of position sensor.

64. An apparatus as claimed claim 50, wherein said voice coil driver is similar to that used in a loud-speaker.

65. An apparatus as claimed in claim 50, wherein said reference surface positioning means includes a loud-speaker.

66. An apparatus as claimed in claim 65, wherein said loud-speaker is used as or constitutes a displacement driver for the reference surface.

67. An apparatus as claimed in claim 50, wherein the reference surface is mounted on a pendulum including a plurality of substantially parallel sheets of flexible material.

68. An apparatus as claimed in claim 67 for calibrating said laser ablation apparatus for use in ablating a predetermined material, wherein said sample has an ablation rate that is a substantially constant fraction of the ablation rate of said material to be ablated over the range of fluences used in ablating said material.

69. An apparatus as claim 68, wherein said fraction equals 1.0.

70. An apparatus as claimed in claim 68 or 69, wherein said material is biological tissue.

71. An apparatus as claimed in claim 70, wherein said biological tissue is corneal tissue.

72. An apparatus is claimed in either claim 70 or 71, in combination with apparatus for laser ablating said biological tissue in a surgical procedure.

73. An apparatus as claimed in claim 72, wherein said surgical procedure is PRK or LASIK.

74. An apparatus as claimed in claim 70, wherein said fluences are in the range 50–800 mJ/cm$^2$.

75. An apparatus as claimed in claim 74, wherein said fluences are in the range 120–250 mJ/cm$^2$.

76. An apparatus as claimed in claim 50, further including said sample, wherein said sample surface comprises a plastic polymer.

77. An apparatus as claimed in claim 50, wherein the laser source means is for use in PRK or LASIK operations of the cornea of the eye to correct refractive errors.

78. An apparatus as claimed in claim 50, including a corneal topography measuring means for measuring the topography of the front surface of a human or animal eye and communication means for communicating with said topography measuring means, for predicting post laser treatment eye topography from calibration measurements in plastic and topography measurements of the eye.

79. An apparatus as claimed in claim 78, including display means for displaying the post laser treatment corneal topography predicted by means of the apparatus.

80. An apparatus as claimed in claim 50, including laser ablation apparatus, said means for determining said surface profile and for calibrating said laser ablation apparatus being in communication with said laser ablation apparatus for adjusting the calibration and shape controls thereof.

81. An apparatus as claimed in claim 80, wherein the laser ablation apparatus is for use in PRK or LASIK operations of the cornea of the eye to correct refractive errors.

* * * * *